(12) United States Patent
Meng et al.

(10) Patent No.: US 6,719,726 B2
(45) Date of Patent: *Apr. 13, 2004

(54) CATHETER HAVING A LOW DRAG SEPTUM

(75) Inventors: Clement Wan Chye Meng, Singapore (SG); Cheng Kiat Jin, Singapore (SG); Tom M. Miner, Riverton, UT (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/253,682

(22) Filed: Sep. 24, 2002

(65) Prior Publication Data
US 2003/0069542 A1 Apr. 10, 2003

Related U.S. Application Data

(62) Division of application No. 09/865,918, filed on May 25, 2001, now Pat. No. 6,506,181.

(51) Int. Cl.[7] .................. A61M 5/178; A61M 5/32; A61M 5/00; A61M 5/31
(52) U.S. Cl. .................................. 604/164.07
(58) Field of Search ................. 604/164.07, 164.01, 604/164.04, 167.02, 167.04, 167.06, 171, 172, 174, 177, 239, 272, 900

(56) References Cited

U.S. PATENT DOCUMENTS

| | | | |
|---|---|---|---|
| 4,857,062 A | * 8/1989 | Russell | 604/256 |
| 4,895,346 A | 1/1990 | Steigerwald | 251/149 |
| 5,009,391 A | 4/1991 | Steigerwald | 251/149.1 |
| 5,059,186 A | * 10/1991 | Yamamoto et al. | 604/280 |
| 5,064,416 A | * 11/1991 | Newgard et al. | 604/167 |
| 5,176,653 A | 1/1993 | Metais | 604/167 |
| 5,211,634 A | * 5/1993 | Vaillancourt | 604/167 |
| 5,290,222 A | * 3/1994 | Feng et al. | 604/86 |
| 5,352,205 A | * 10/1994 | Dales et al. | 604/158 |
| 5,575,777 A | * 11/1996 | Cover et al. | 604/198 |
| 5,697,914 A | * 12/1997 | Brimhall | 604/177 |
| 5,810,780 A | * 9/1998 | Brimhall et al. | 604/167 |
| 5,935,110 A | * 8/1999 | Brimhall | 604/167 |
| 6,206,851 B1 | 3/2001 | Prosl | 604/93 |
| 6,224,569 B1 | * 5/2001 | Brimhall | 604/164 |
| 6,228,060 B1 | * 5/2001 | Howell | 604/167.04 |
| 6,506,181 B2 | * 1/2003 | Meng et al. | 604/164.07 |
| 2001/0053895 A1 | * 12/2001 | Vaillancourt | 604/243 |
| 2002/0072712 A1 | * 6/2002 | Nool et al. | 604/167.01 |

FOREIGN PATENT DOCUMENTS

EP   0 268 480 A1   5/1988

* cited by examiner

*Primary Examiner*—Eduardo C. Robert
*Assistant Examiner*—Anuradha Ramana
(74) *Attorney, Agent, or Firm*—James J. Murtha

(57) ABSTRACT

The catheter and introducer needle assembly of this invention includes a catheter adapter at its proximal end having a hollow septum disposed therein. The septum preferably is hollow to minimize drag as the introducer needle is removed therefrom. If desired a gel or lubricious material may be disposed in the cavity.

11 Claims, 11 Drawing Sheets

CATHETER HAVING A LOW DRAG SEPTUM

This application is a Division of Ser. No. 09/865,918 filed May 25, 2001 now U.S. Pat. No. 6,506,181.

BACKGROUND OF THE INVENTION

This invention relates to a catheter and introducer needle assembly. Catheters, particularly intravenous (IV) catheters, are used for infusing fluid, such as normal saline solution, various medicaments and total parenteral nutrition, into a patient, withdrawing blood from a patient or monitoring various parameters of the patient's vascular system. Peripheral IV catheters tend to be relatively short, and typically are on the order of about two inches or less in length. The most common type of IV catheter is an over-the-needle peripheral IV catheter. As its name implies, an over-the-needle IV catheter is mounted over an introducer needle having a sharp distal tip. At least the distal portion of the catheter tightly engages the outer surface of the needle to prevent peelback of the catheter and thus facilitates insertion of the catheter into the blood vessel. The distal tip of the introducer needle extends beyond the distal tip of the catheter with the bevel of the needle facing up away from the patient's skin.

The catheter and introducer needle assembly is inserted at a shallow angle through the patient's skin into a blood vessel. There are many techniques for inserting such a catheter and introducer needle assembly into a patient. In one insertion technique, the introducer needle and catheter are inserted completely into the blood vessel together. In another technique, the introducer needle is partially withdrawn into the catheter after the initial insertion into the blood vessel. The catheter is then threaded over the needle and inserted completely into the blood vessel.

In order to verify proper placement of the catheter in the blood vessel, the clinician confirms that there is flashback of blood in a flashback chamber. The flashback chamber is typically formed as part of the needle hub. Alternatively, the introducer needle could include a notch or opening formed along a distal portion thereof so that the blood flashback can be observed in the annular space between the introducer needle and the catheter when the catheter is transparent or at least translucent. Once proper placement of the catheter into the blood vessel is confirmed, the clinician applies pressure to the blood vessel by pressing down on the patient's skin over the blood vessel distal of the introducer needle and the catheter. This finger pressure occludes or at least minimizes further blood flow through the introducer needle and the catheter. The clinician then withdraws the introducer needle, leaving the catheter in place, and attaches an appropriate device to the catheter. Such a device can include a fluid delivery device, a PRN, a deadender cap or a blood pressure monitoring probe.

Although typical IV catheter and introducer needle assemblies generally perform their functions satisfactorily, they do have certain drawbacks. For example, the procedure for properly placing a catheter into a patient's blood vessel can result in a significant amount of blood leakage from the catheter between the initial venipuncture and the time that an appropriate device is connected to the catheter. This blood leakage is problematic because of potential contamination to a clinician from an infected patient. This is especially worrisome because of the advent of currently incurable and fatal diseases, such as Acquired Immune Deficiency Syndrome ("AIDS"), which can be transmitted by the exchange of body fluids from an infected person to another person. Thus, contact with the body fluid of an AIDS infected person must be avoided.

In order to minimize blood leakage, it is known to include a self-sealing septum placed in the proximal end of the catheter hub. The septum allows the introducer needle to extend through the septum and the catheter to allow the catheter to be placed into a patient's blood vessel. In addition, the septum allows the clinician to withdraw the introducer needle from the catheter and the septum, which then closes after the introducer needle has been completely withdrawn from the catheter hub. This arrangement does minimize blood leakage from the catheter hub. However, the use of a septum significantly increases the force that the clinician needs to exert on the introducer needle in order to withdraw the introducer needle from the catheter. In addition, if the introducer needle is located in the septum for extended periods of time, such as when the catheter is in a healthcare facility's inventory prior to use, the septum may take a compression set about the introducer needle. This may prevent the septum from completely sealing once the introducer needle is ultimately withdrawn from the septum, which is antithetical to the use of the septum in the first place. In addition, where an introducer needle is used that includes a notch formed therein, blood leakage could still occur when the introducer needle is being withdrawn from the catheter if the septum is not properly configured.

SUMMARY OF THE INVENTION

It is therefore an object of this invention to provide an IV catheter and introducer needle assembly that minimizes blood leakage from the assembly during the insertion procedure.

It is another object of this invention to provide an IV catheter and introducer needle assembly that uses a septum to minimize blood leakage from the assembly even where a notched introducer needle is used.

It is still another object of this invention to provide an IV catheter and introducer needle assembly that uses a septum to minimize blood leakage from the assembly but that exerts a reduced drag force on the introducer needle when it is being withdrawn from the catheter.

It is yet a further object of this invention to provide an IV catheter and introducer needle assembly that uses a septum to minimize blood leakage from the assembly and that does not take a compression set about the needle so the septum effectively blocks the flow of fluid therethrough even after the introducer needle is removed from the catheter.

The above and other objects are satisfied by the IV catheter and introducer needle assembly with the low drag septum of this invention. The catheter assembly includes an adapter at its proximal end, which preferably includes at least one wing radially extending from the catheter adapter. The catheter adapter also includes a side port in fluid communication with the catheter. A septum is located in the proximal end of the catheter adapter proximal of the side port. The septum prevents any fluid from flowing into or out of the proximal end of the catheter adapter and thus diverts any fluid flowing in the catheter lumen into the side port. The septum has a hollow interior portion to minimize drag on the introducer needle as it is being withdrawn from the catheter through the septum.

The introducer needle is connected at its proximal end to a needle hub and preferably includes at least one notch, i.e. a hole or opening in the sidewall, formed therein in communication with the introducer needle lumen. The notch is formed in the introducer needle such that blood can flow into the open distal end of the introducer needle, through the lumen in the introducer needle and through the notch outside the introducer needle into the catheter lumen. Thereafter, the blood can flow through the annular space between the outside of the introducer needle and the inside of the catheter and catheter adapter and then through the side port and extension tube that extends from the catheter adapter. Preferably, the catheter, the catheter adapter and the extension tube are transparent or at least translucent. In this way, the clinician can immediately and easily visualize flashback of blood through these parts of the catheter assembly when the introducer needle has been inserted into a patient's blood vessel.

After the clinician confirms proper placement of the catheter into the patient's blood vessel, the clinician withdraws the introducer needle from the catheter by pulling the needle hub in a proximal direction. The septum must be long enough so that both the notch and the open distal end of the introducer needle can be located simultaneously within the septum. This ensures no blood leakage occurs when the introducer needle is being withdrawn from the catheter. If the septum is too short, the open distal end of the introducer needle could be distal of the distal end of the septum in the blood flow path while the notch could be located proximal of the proximal end of the septum. This could allow blood to leak form the catheter when the introducer needle is being withdrawn. The septum defines a hollow internal portion which minimizes drag on the introducer needle as it is being withdrawn therefrom.

BRIEF DESCRIPTION OF THE DRAWINGS

The above and other objects and advantages will be apparent upon consideration of the following drawings and detailed description. The preferred embodiments of the present invention are illustrated in the appended drawings in which like reference numbers refer to like elements and in which.

DETAILED DESCRIPTION OF THE INVENTION

Figure 1:
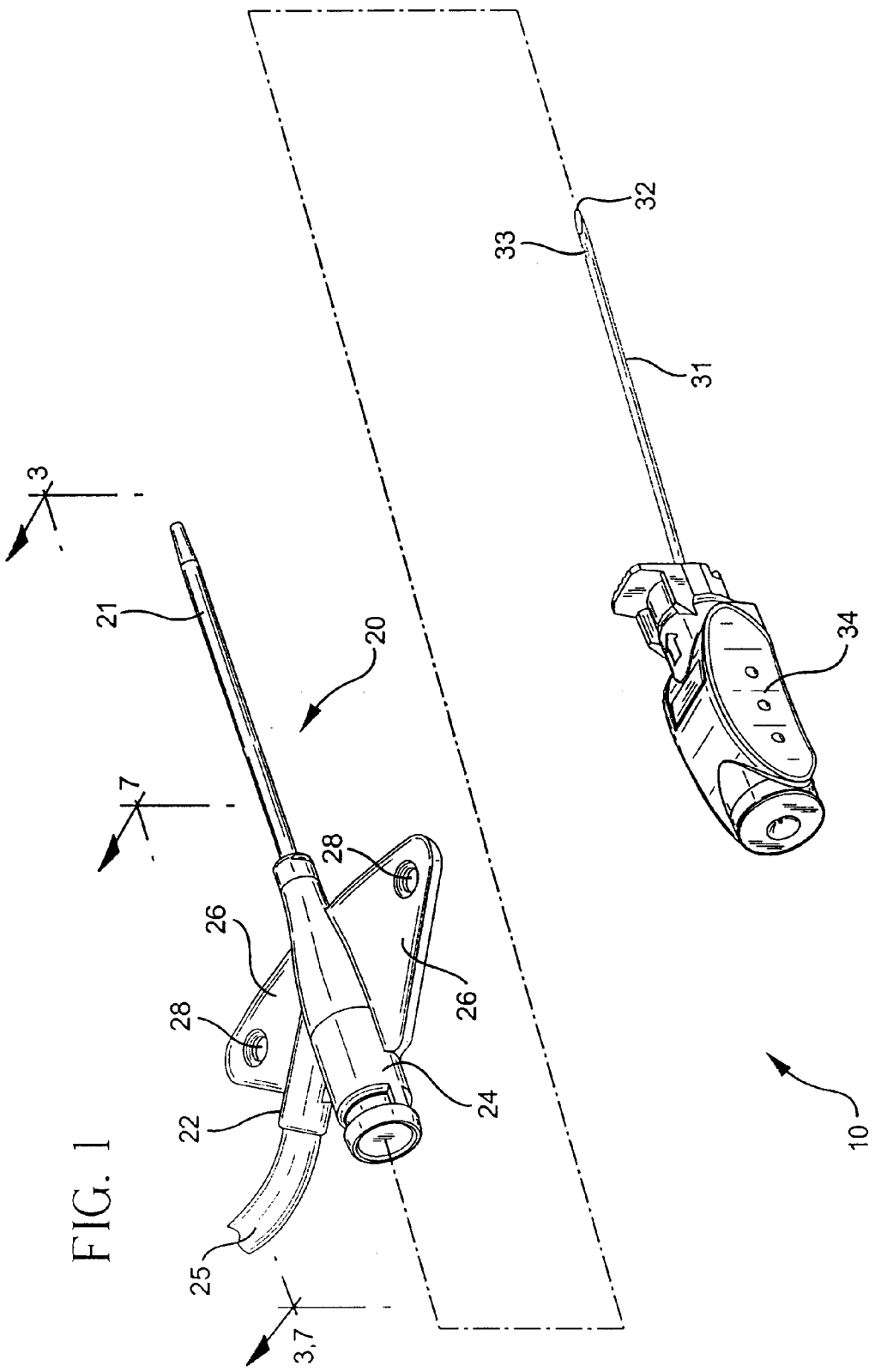
FIG. 1 is a perspective view of an integrated catheter and introducer needle having the low drag septum of this invention.
Figure 2:
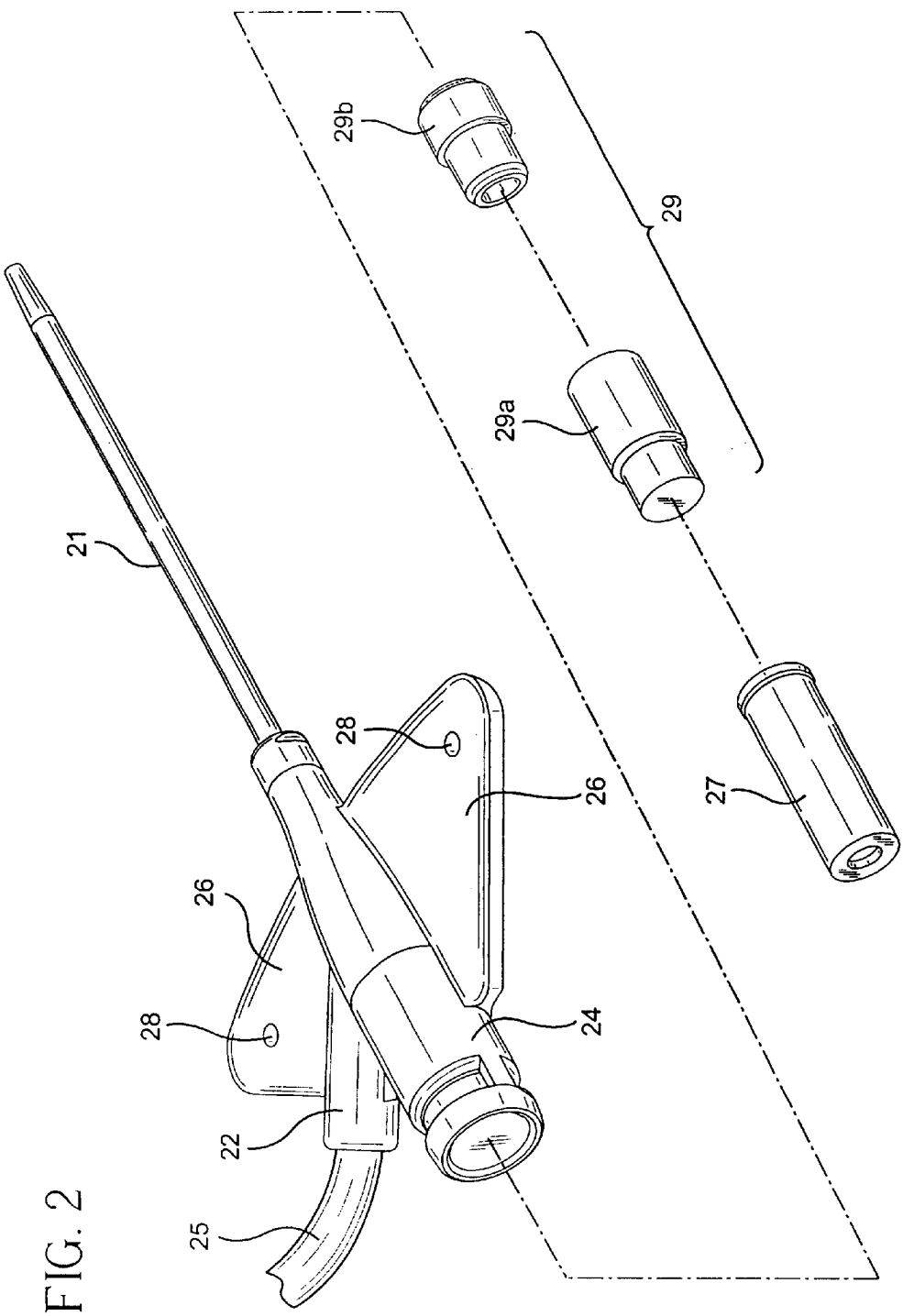
FIG. 2 is an exploded perspective view of an integrated catheter assembly having the low drag septum of this invention.
Figure 3:
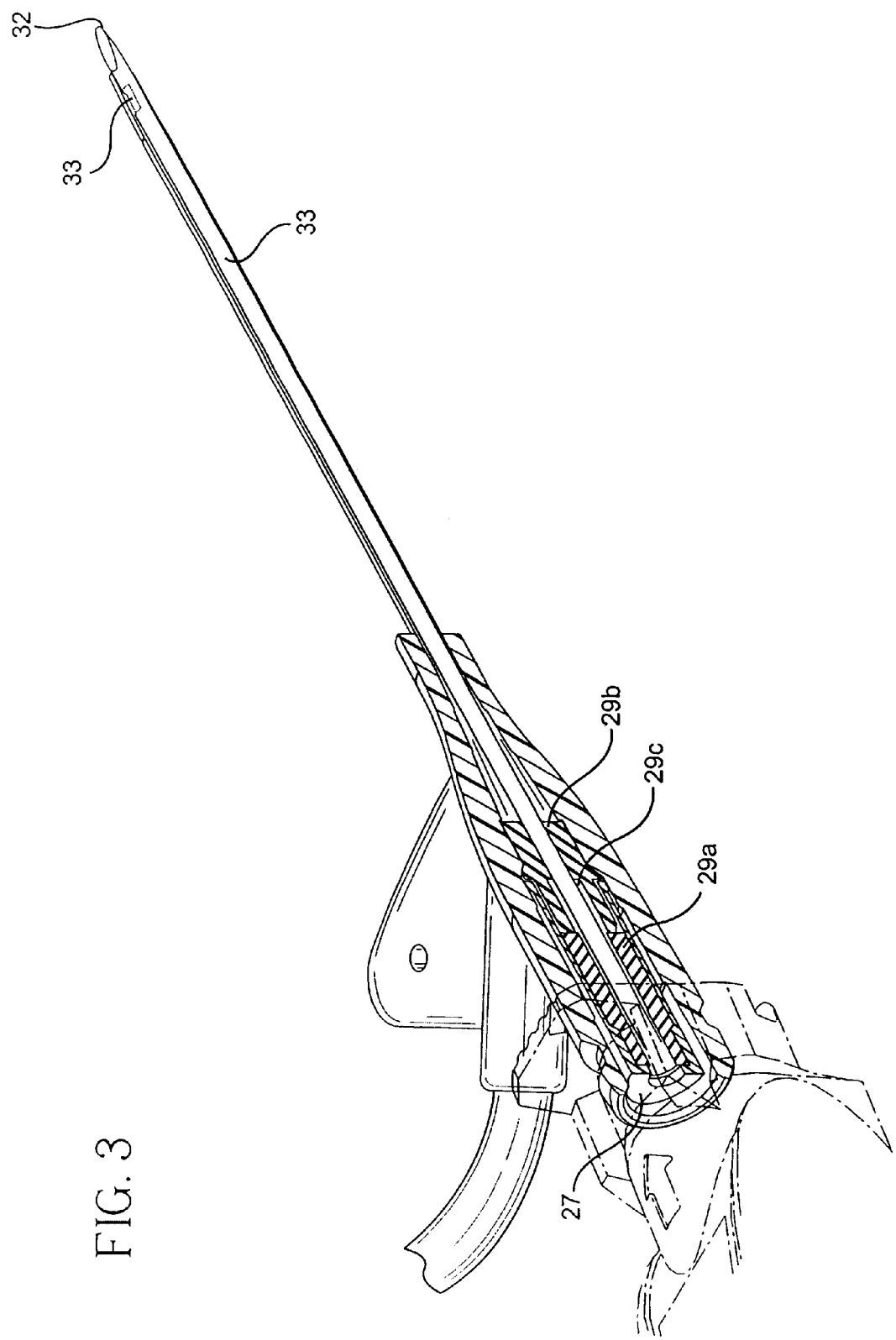
FIG. 3 is a perspective cross-sectional view of the invention taken along line 3—3 in FIG. 1 showing the catheter and introducer needle assembly having a first embodiment of the low drag septum of this invention, with a portion of the introducer needle assembly in phantom, prior to insertion into a patient.

As used herein, the term "proximal" refers to a location with respect to the device that, during normal use, is closest to the clinician using the device and farthest from the patient in connection with whom the device is used. Conversely, the term "distal" refers to a location with respect to the device that, during normal use, is farthest from the clinician using the device and closest to the patient in connection with whom the device is used.

As used herein, the term "top", "up" or "upwardly" refers to a location with respect to the device that, during normal use, is radially away from the longitudinal axis of the device and away from the patient's skin. Conversely, as used herein, the term "bottom", "down" or "downwardly" refers to a location with respect to the device that, during normal use, is radially away from the longitudinal axis of the device and toward the patient's skin.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

This invention is described herein using like reference numbers for like elements in the different embodiments. Although this invention is described herein in connection with a peripheral IV catheter having an integrated extension tube (an "integrated catheter"), it is to be understood that this invention is applicable to other catheters. For example, this invention is applicable to standard peripheral IV catheters, extended dwell catheters requiring the needle to be connected to the needle hub by a stylet as well as other medical devices where it is desirable to include a septum to regulate the flow of fluid into or out of a space. In addition, while this invention is satisfied by embodiments in many different forms, there are shown in the drawings and herein described in detail, preferred embodiments of the invention with the scope of the invention measured by the appended claims.

An integrated catheter and introducer needle assembly including the low drag septum of this invention is shown generally at 10 in FIG. 1. The catheter assembly 20 includes catheter 21 affixed to catheter adapter 24. Suitable materials for catheter 21 include, but are not limited to, thermoplastic resins such as fluorinated ethylene propylene (FEP), polytetrafluoroethylene (PTFE), polyurethane and the like. Preferably, catheter 21 is formed from a thermoplastic hydrophilic polyurethane that softens with exposure to physiological conditions present in the patient's body. In addition, the material used to form catheter 21 is preferably transparent or at least translucent. This allows the clinician to see blood flashback in the annular space between the introducer needle and catheter 21 where the introducer needle includes a notch or opening adjacent to its distal end to allow such blood flow. Suitable materials for catheter adapter 24 include, but are not limited to, thermoplastic polymeric resins such as polycarbonate, polystyrene, polypropylene and the like. Preferably the material used to form catheter adapter 24 is transparent or at least translucent to allow the clinician to view blood flashback therein.

Catheter adapter 24 includes a side port 22, which has an extension tube 25 connected thereto. Preferably, extension tube 25 is preferably formed from a translucent material such as polyvinyl chloride, polyurethane and the like to facilitate visualization of blood flashback through extension tube 25. The proximal end (not shown) of extension tube 25 may include a standard luer lock adaptor or other fluid access device to allow the connection of an IV fluid supply line to extension tube 25. Such an IV fluid supply line can be connected to extension tube 25 prior to insertion of assembly 10 into a patient. Side port 22 is in fluid communication with the lumen of catheter 21 so that fluid infused through extension tube 25 will pass into the patient once catheter 21 is properly positioned in the patient. Conversely, blood exiting a patient's vein through catheter 21 can travel through extension tube 25.

Catheter adapter 24 may also include a pair of wings 26 that extends radially outwardly from either side of catheter adapter 24. Wings 26 are preferably located adjacent to sideport 22 below the main body portion of catheter adapter 24. Wings 26 facilitate manipulation of catheter assembly 20 and enhance patient comfort when catheter assembly 20 is affixed to the patient. Wings 26 may include suture holes 28 to facilitate fixation of catheter assembly 20 to the patient.

The proximal end of catheter adapter 24 is sealed with a septum 29 to ensure that fluid does not leak out of the proximal end of catheter adapter 24. Preferably, septum 29 is formed from two portions, a proximal portion 29a and a distal portion 29b, each of which is pre-slit to facilitate locating an introducer needle 31 therethrough. Septum distal portion 29b provides the primary seal preventing fluid flow past septum 29 while septum proximal portion 29a provides a secondary seal. Although septum 29 could be formed from one piece, two pieces are used because it is easier and less expensive to manufacture. In addition, forming septum 29 from two separate pieces increases the column strength and facilitates assembly into catheter adapter 24. Preferably septum distal portion 29b and septum proximal portion 29a are formed from the same material and have the same hardness. Suitable materials for septum 29 include a peroxide cured elastomer such as polyisoprene, silicone and the like where the materials have a durometer in the range of 35–45 Shore A. Preferably a septum housing 27 having an open proximal end and an open distal end surrounds at least a portion of septum proximal portion 29a and septum distal portion 29b in an interference fit to hold septum 29 in place in position in catheter adapter 24. Alternatively, septum 29 could be located in catheter adapter 24 without the use of housing 27. However, housing 27 facilitates placement of septum 29 in catheter adapter 24. As shown in the FIGS., housing 27 extends only along the proximal portion of septum distal portion 29b. However, if desired, housing 27 could extend completely along the entire length of septum 29 or just along septum distal portion 29b. With such a configuration, it is to be understood that housing 27 would be configured so it would apply the desired compressive force to septum 29 instead of catheter adapter 24 as discussed below. The open proximal and distal ends of housing 27 allow an introducer needle 31 to extend through septum 29 past housing 27. Preferably the proximal end of housing 27 abuts and extends over a portion of the surface area of the proximal face of septum 29. This configuration prevents the attachment of another medical device to the proximal end of catheter adapter 24. Instead any such medical device that should be connected to catheter adapter 24 would be connected to the fluid access device (not shown) located at the proximal end of extension tube 25.

Septum 29 and septum housing 27 are located in catheter adapter 24 so that at least the distal portion of septum distal portion 29b engages the inside of catheter adapter 24. The external diameter of at least the distal portion of septum distal portion 29b is greater than the internal diameter of catheter adapter 24 at least along the portion that engages the distal portion of septum distal portion 29b. Preferably, the external diameter of the distal portion of septum distal portion 29b should be at least 5% larger than the internal diameter of the relevant portion of catheter adapter 24. With this configuration, catheter adapter 24 exerts a radial compressive force against distal portion 29b. This compressive force helps to hold housing 27 in place and also helps to seal septum distal portion 29b after introducer needle 31 has been withdrawn from septum 29 so that septum distal portion 29b does not take a compression set about introducer needle 31. The portion of catheter adapter 24 that engages septum distal portion 29b should be arranged such that the proximal end of septum 29 is adjacent to the open proximal end of catheter adapter 24 when catheter adapter 24 engages septum distal portion 28b. Septum housing 27 and septum 29 could also be affixed inside catheter adapter 24 using an alternate technique such as by an interference fit between housing 27 and catheter adapter 24, the use of an adhesive or by ultrasonic welding.

Figure 7:
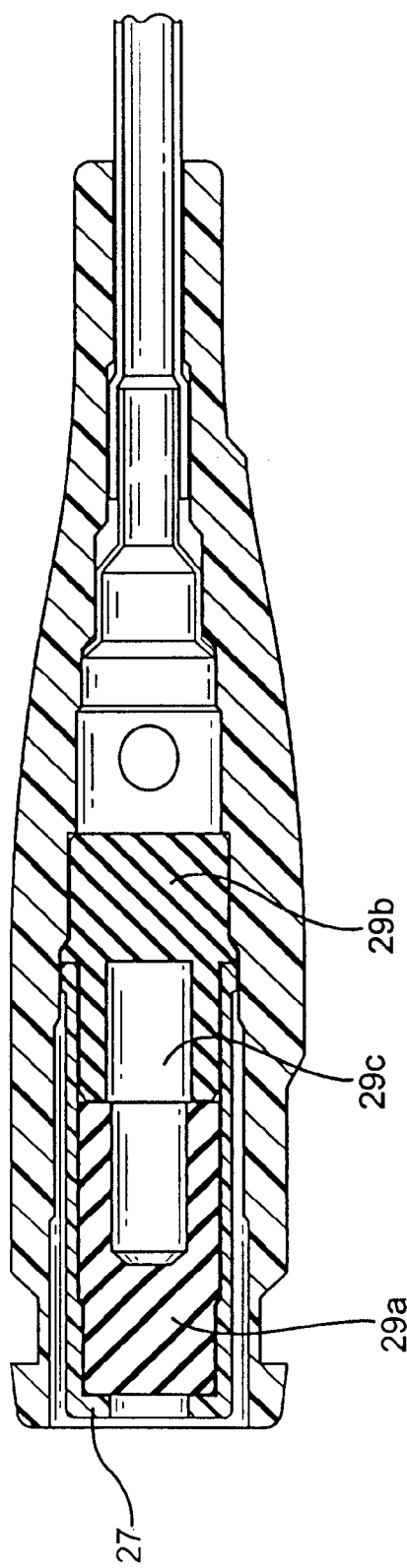
FIG. 7 is a cross-sectional view of a portion of the integrated catheter having the low drag septum of this invention taken along line 7—7 in FIG. 1 without the introducer needle assembly showing the configuration of the first embodiment of the low drag septum of this invention disposed in the catheter.
Figure 8:
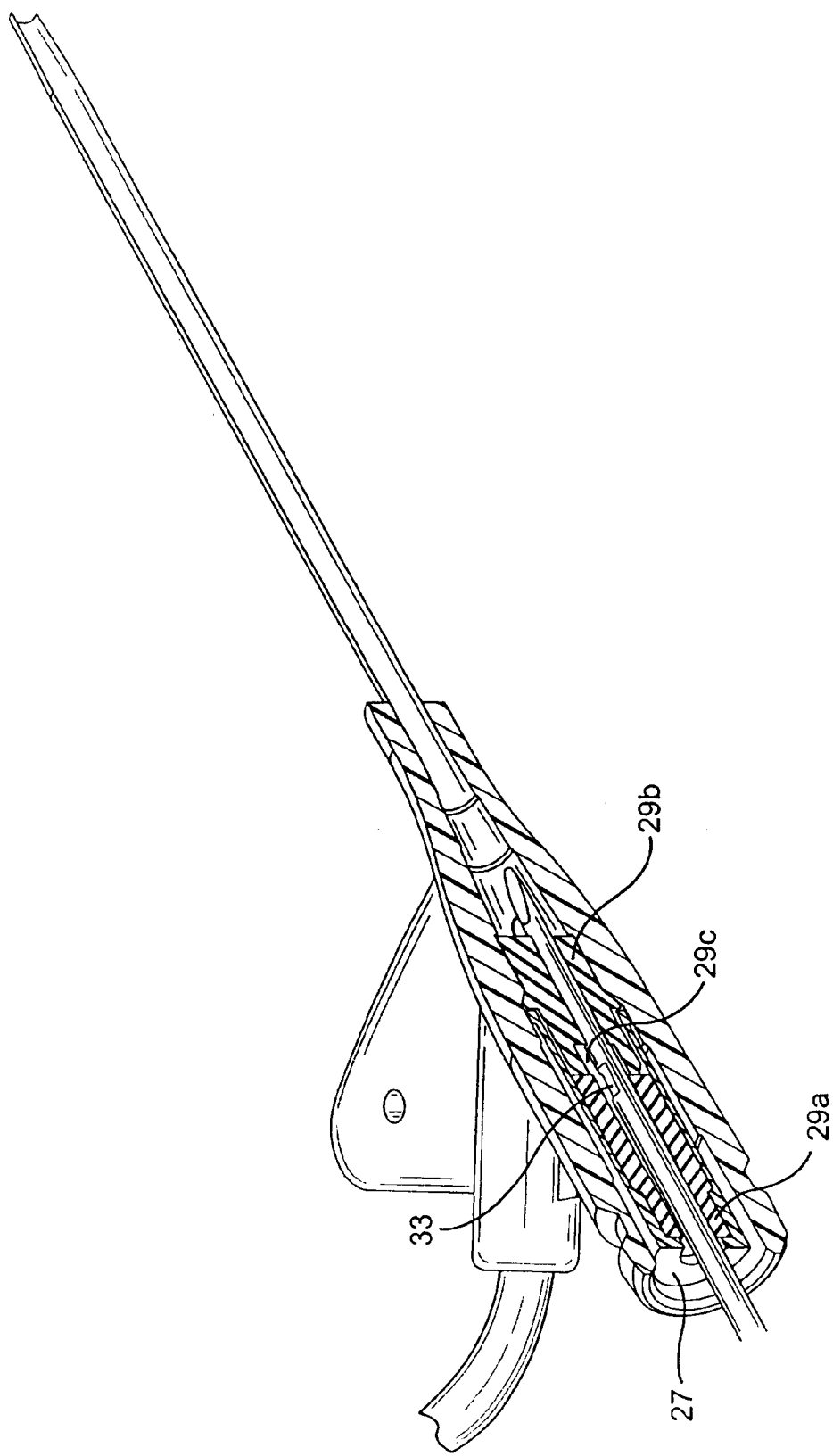
FIG. 8 is a perspective cross-sectional view of the catheter and introducer needle assembly similar to FIG. 3 but showing a different relationship between the introducer needle and the low drag septum of this invention where the distal tip of the introducer needle is distal of the distal end of the septum.
Figure 9:
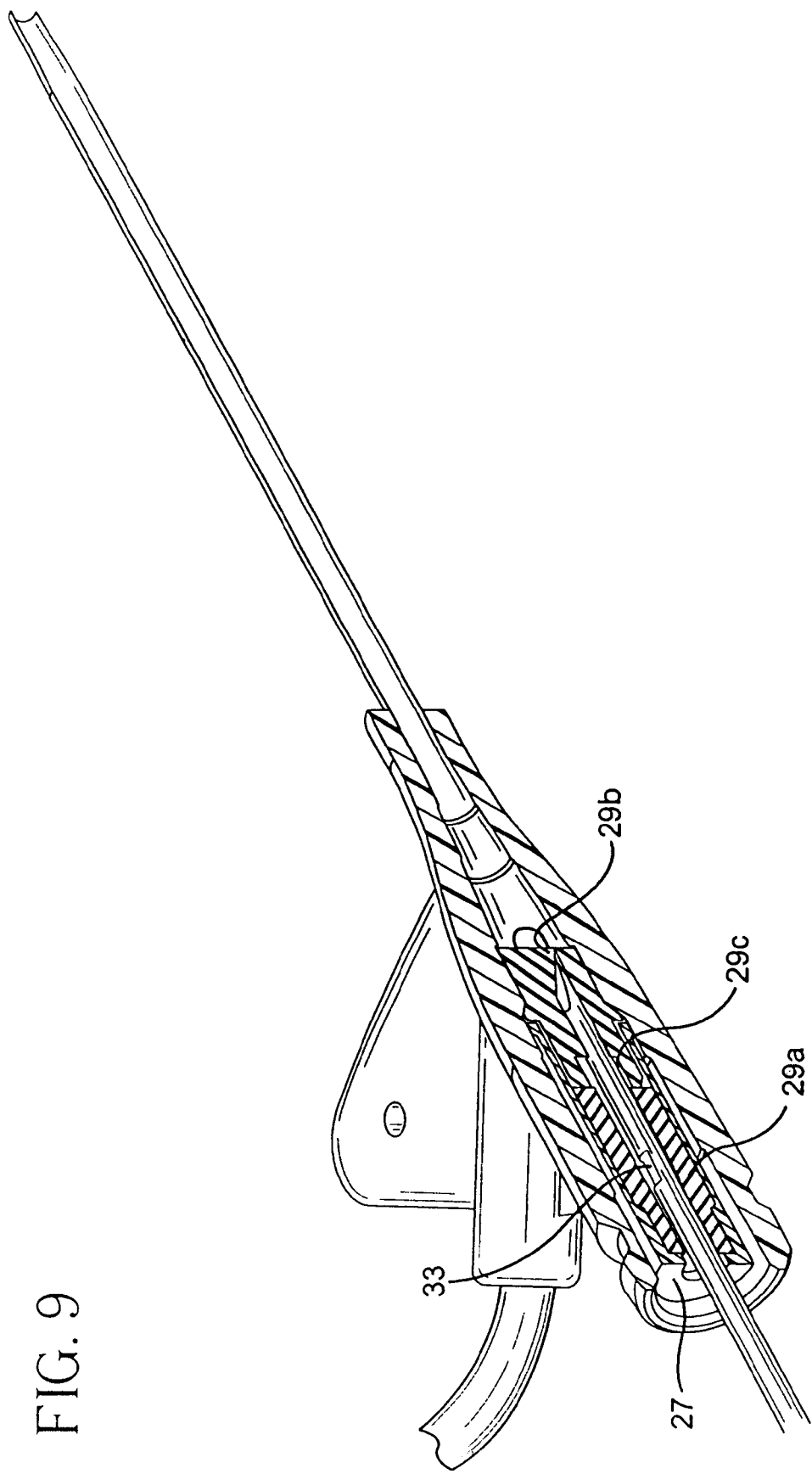
FIG. 9 is a perspective cross-sectional view of the catheter and introducer needle assembly similar to FIG. 4 but showing a different relationship between the introducer needle and the low drag septum of this invention where the distal tip of the introducer needle is disposed in the distal portion of the septum.
Figure 10:
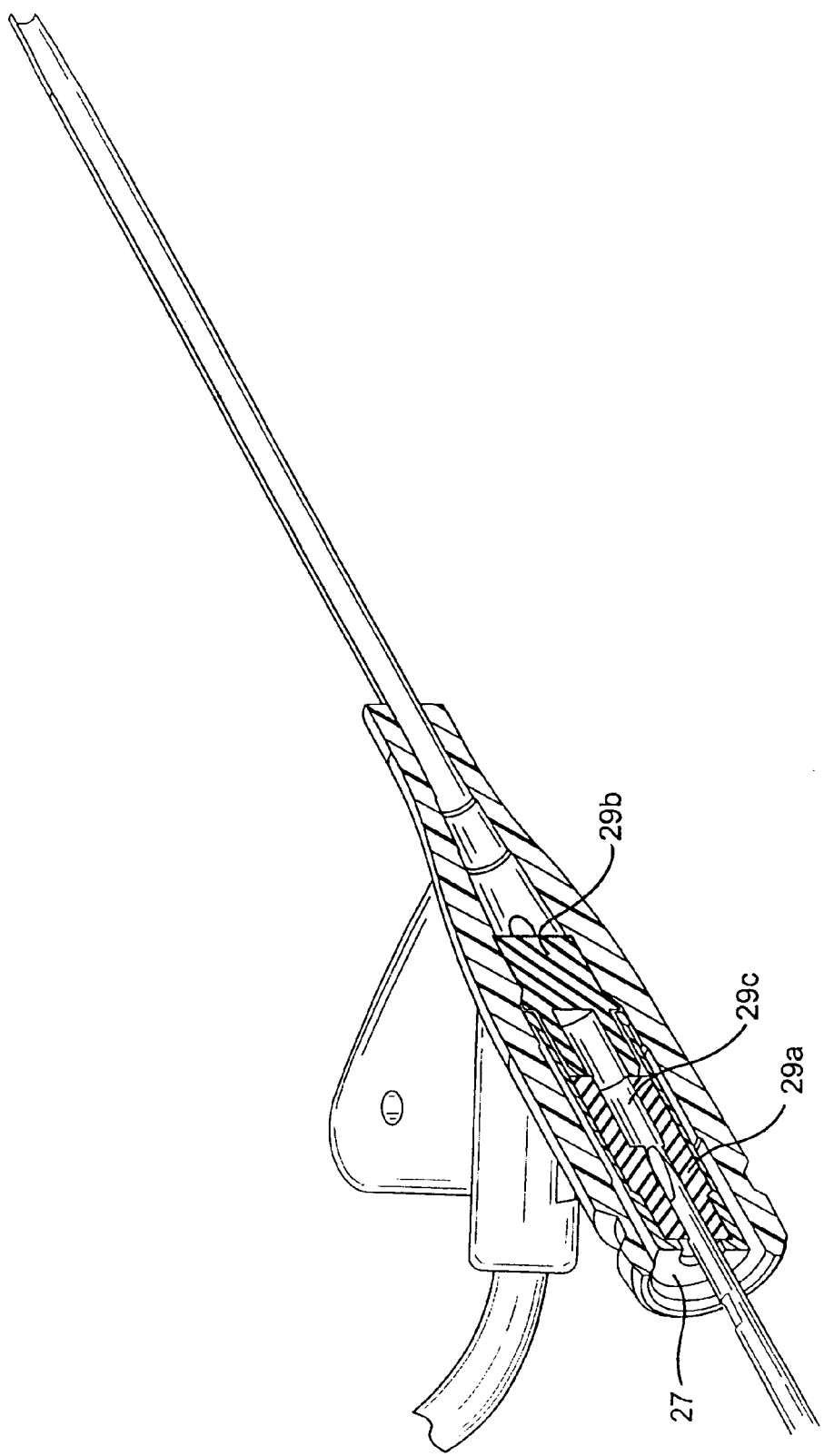
FIG. 10 is a perspective cross-sectional view of the catheter and introducer needle assembly similar to FIG. 5 but showing a different relationship between the introducer needle and the low drag septum of this invention where the distal tip of the introducer needle is disposed in the proximal portion of the septum.
Figure 11:
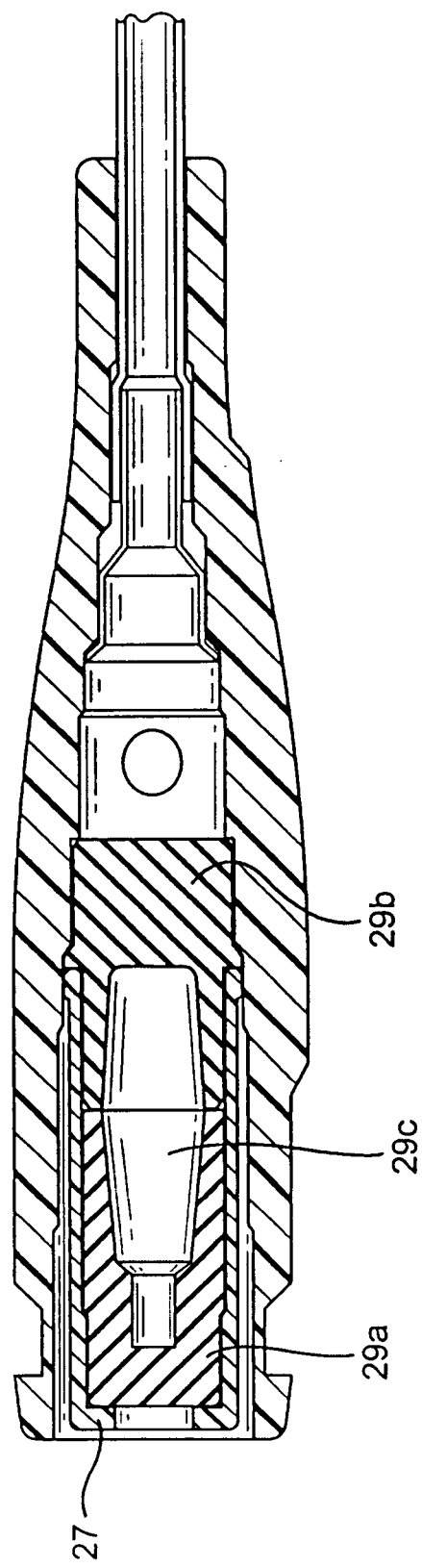
FIG. 11 is a cross-sectional view similar to the view in FIG. 7 of a portion of the integrated catheter having the low drag septum of this invention but showing the configuration of the second embodiment of the low drag septum of this invention disposed in the catheter

Septum 29 defines a cavity or hollow interior portion 29c formed between septum proximal portion 29a and septum distal portion 29b. This minimizes drag on introducer needle 31 as it is being withdrawn from catheter assembly 20. Testing of septum 29 against a standard septum shows that the average drag force for septum 29 with hollow interior portion 29c is about 0.15 pounds while the average drag force for a septum without a hollow interior is about 0.30 pounds. Hollow interior portion 29c should be sized to minimize drag but it must not be too large so that it acts as a reservoir for microbial growth therein if fluid were to become trapped therein. Hollow interior portion 29c could have a cylindrical configuration such as shown in FIG. 7. However, preferably hollow interior portion 29c has a configuration such as shown in FIG. 11 where the proximal section is generally cylindrical, the medial section is tapered such that it increases in diameter in the distal direction, and the distal section is tapered such that it decreases in diameter in the distal direction. Preferably the taper should be between about 2 degrees and about 10 degrees to the horizontal plane. This configuration reduces the volume of dead space which could become a reservoir for blood when introducer needle 31 is withdrawn from catheter 21. Thus the cross section of hollow interior portion 29c should closely approximate the cross section of the largest needle that would be used for introducer needle 31. Preferably, hollow interior portion 29c is between about 6 and about 8 millimeters in length. If desired, hollow interior portion 29c could be filled with some material to prevent unwanted material from becoming trapped therein. If a lubricious material such as a silicone liquid or gel is disposed in hollow interior portion 29c that material could also serve to enhance the drag-reducing characteristic of septum 29.

Where septum 29 is used in connection with introducer needle 31 having notch 33 therein, septum 29 should be longer than the distance between the distal end of introducer needle 31 and the proximal end of notch 33. This prevents blood from leaking out of catheter assembly 20 when introducer needle 31 is being withdrawn therefrom. As shown in FIG. 8, during withdrawal of introducer needle 31, when the distal end of introducer needle 31 is distal of septum distal portion 29b and notch 33 is located in hollow interior portion 29c blood can flow into introducer needle 31 and into hollow interior portion 29c but blood cannot flow out of catheter assembly 20 because of the proximal portion of septum proximal portion 29a. As shown in FIG. 9, during withdrawal of introducer needle 31, when the distal end of introducer needle 31 is located in the distal portion of septum distal portion 29b there is no longer a blood flow path through introducer needle 31 and thus blood can not escape from catheter assembly 20. Finally, as shown in FIG. 10, continued withdrawal of introducer needle 31 allows the proximal portion of septum proximal portion 29a to wipe introducer needle 31 of any residual blood that may be disposed thereon.

Figure 4:
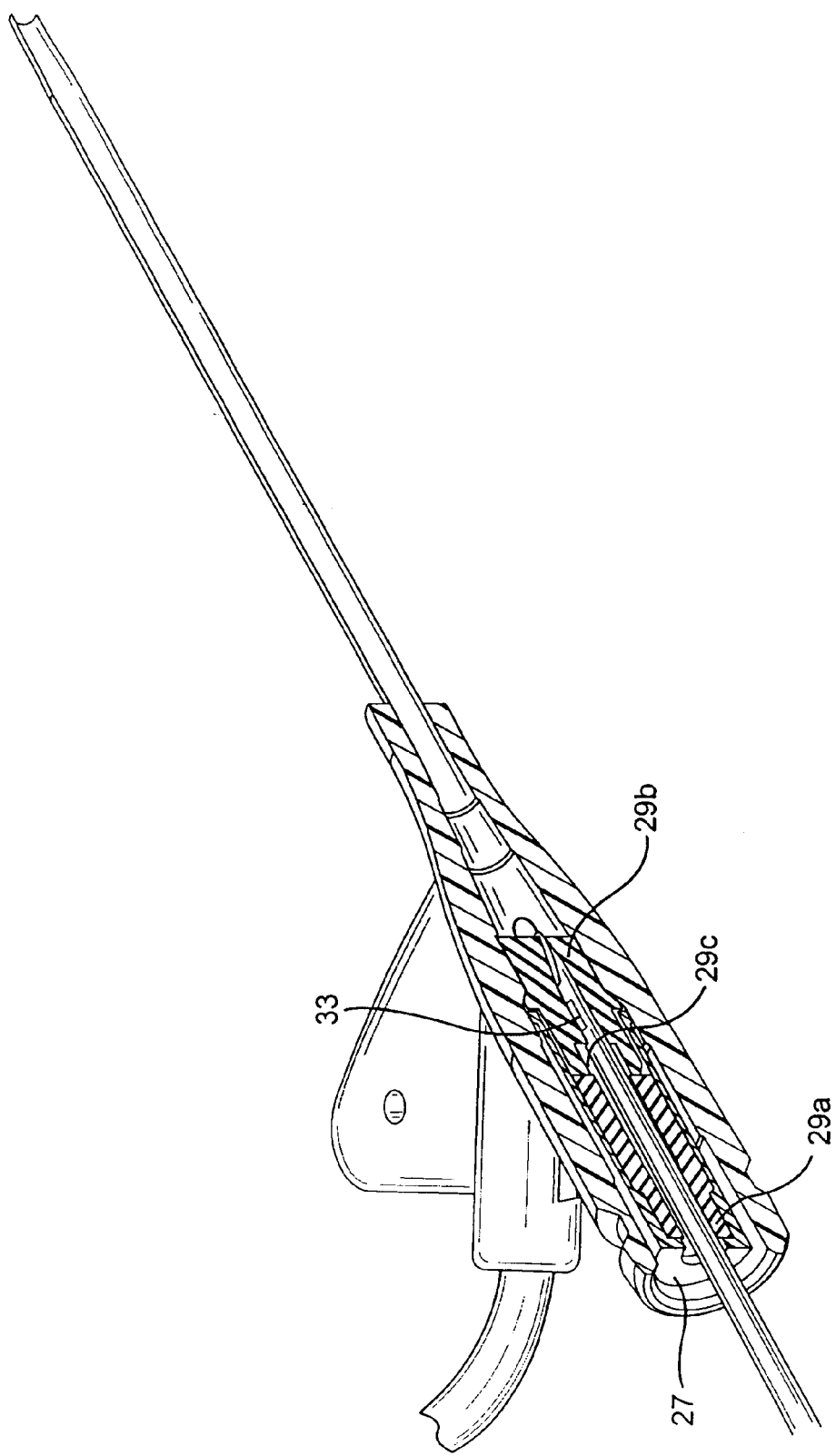
FIG. 4 is a perspective cross-sectional view of the invention similar to the view of FIG. 3 after the catheter assembly has been inserted into a patient but before the introducer needle has been completely retracted from the catheter assembly with the distal portion of the introducer needle disposed in the distal portion of the septum.
Figure 5:
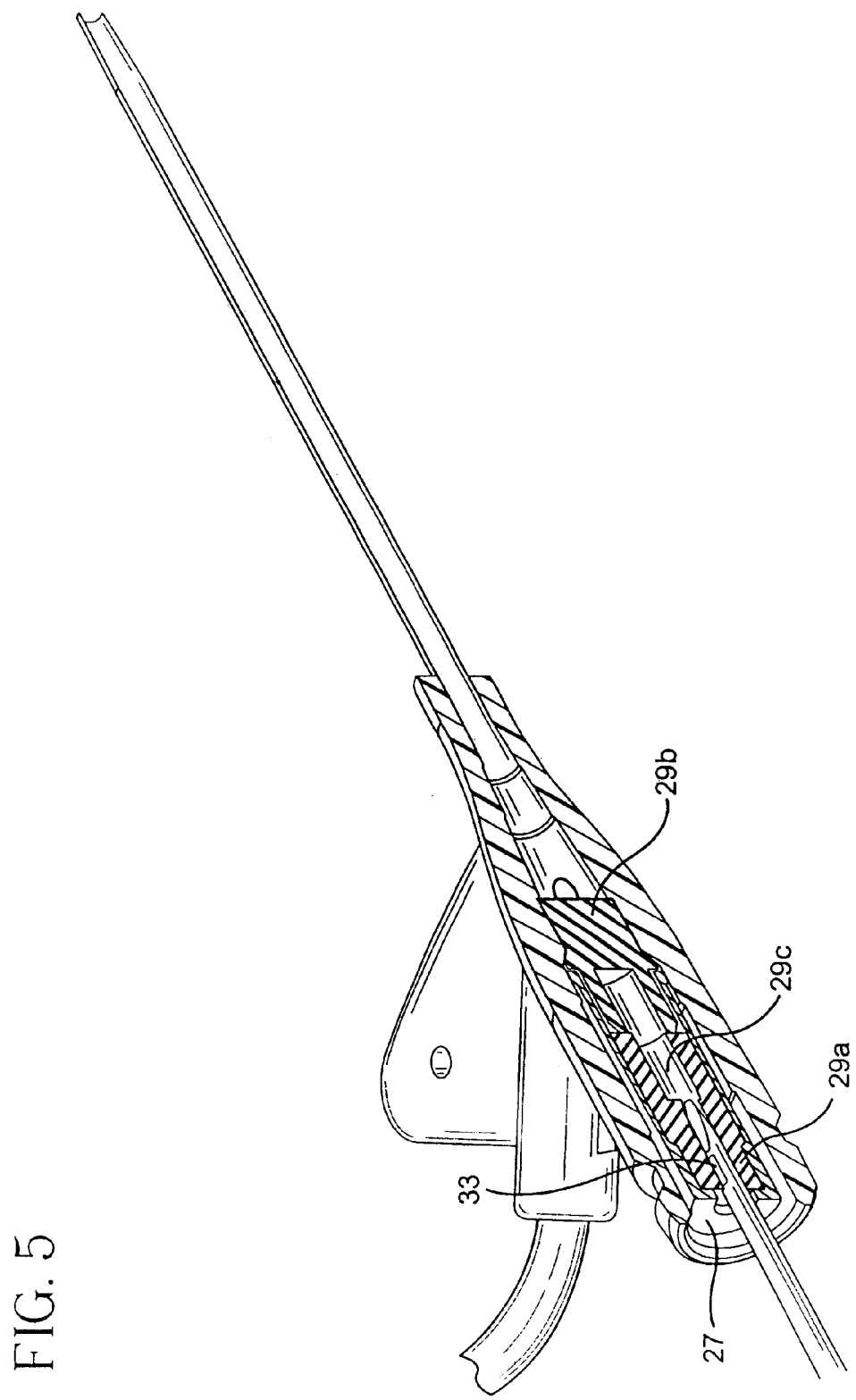
FIG. 5 is a perspective cross-sectional view of the invention similar to the view of FIG. 3 after the catheter assembly has been inserted into a patient but before the introducer needle has been completely retracted from the catheter assembly with the distal portion of the introducer needle disposed in the proximal portion of the septum.
Figure 6:
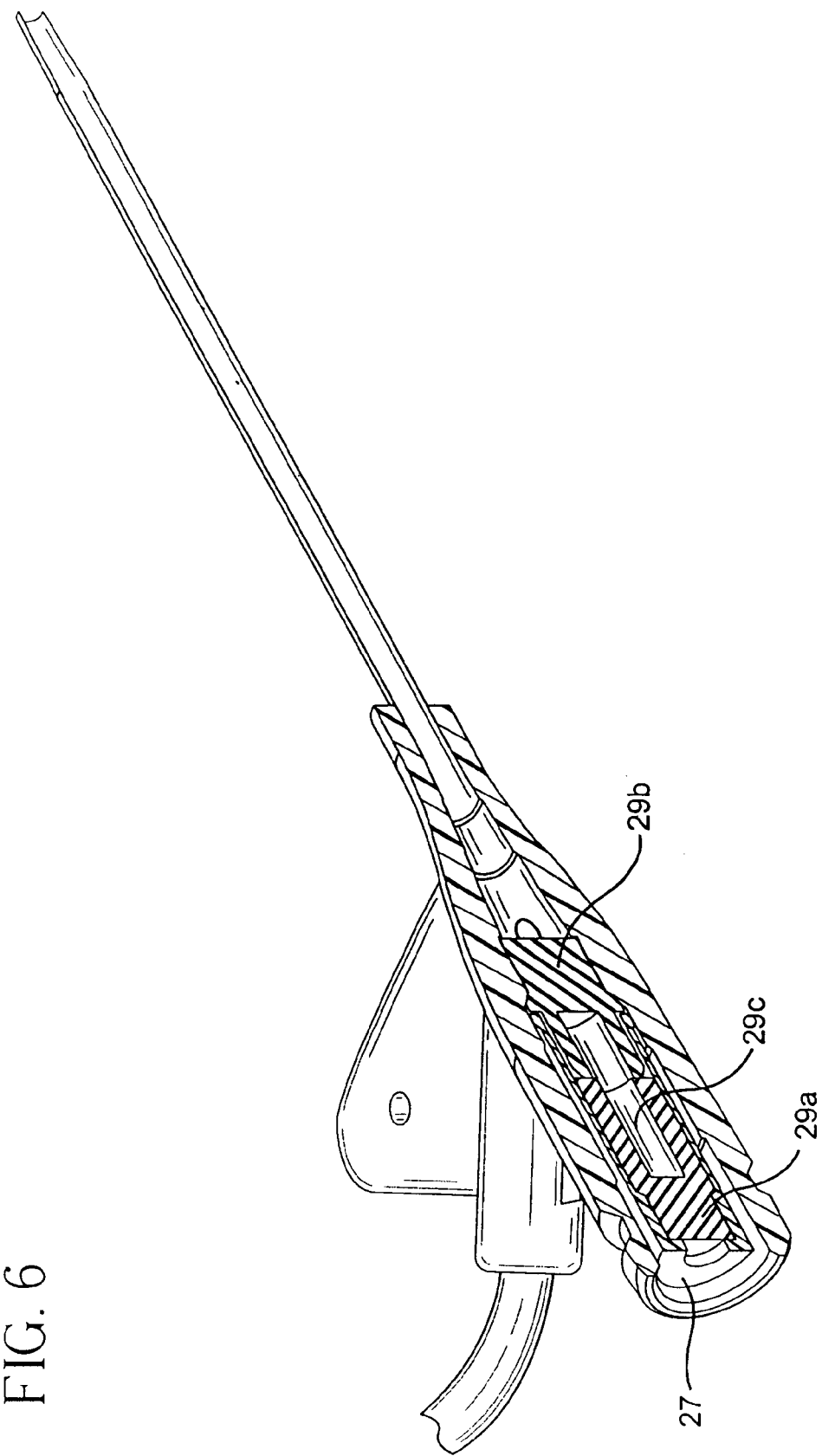
FIG. 6 is a perspective cross-sectional view of the invention similar to the view of FIG. 3 after the catheter assembly has been inserted into a patient with the introducer needle completely retracted from the catheter.

Alternatively, the proximal portion of septum proximal portion 29a and the distal portion of septum distal portion 29b could each be at least as long as the distance between the distal tip of introducer needle 31 and the proximal end of notch 33 formed in the sidewall of introducer needle 31. See FIGS. 4 and 5. This dimension ensures that no flow path is created through introducer needle 31 between the proximal and distal sides of either septum distal portion 29b or septum proximal portion 29a. This will thus minimize blood leakage into hollow interior portion 29c as introducer needle 31 is removed from septum distal portion 29b.

In order to minimize drag on introducer needle 31, the distal portion of septum distal portion 29b and the proximal portion of septum proximal portion 29a should not be longer than about 3 millimeters. Preferably, the distal portion of septum distal portion 29b should be between about 2 and about 3 millimeters long while the proximal portion of septum proximal portion 29a should be between about 1 and about 2.5 millimeters long.

Introducer needle assembly 30 includes introducer needle 31 having a sharp distal tip 32 defined by a bevel and a proximal end connected to a needle hub 34. Introducer needle 31 is preferably formed from stainless steel and has a longitudinal axis that is generally parallel to the longitudinal axis of catheter and introducer needle assembly 10. Introducer needle 31 may be formed with notch 33, i.e. a hole or opening in the sidewall, adjacent to the distal end to allow blood to flow into the open distal end of introducer needle 31 and then out of notch 33 into the annular space between catheter 21 and introducer needle 31. If catheter 21 is at least translucent, the clinician will be able to observe blood flashback promptly upon successful venipuncture. In addition, when the blood flows into extension tube 25, and if extension tube 25 is at least translucent, the clinician will also be able to observe blood flashback there. If desired, and where no notch is formed in introducer needle 31, needle hub 34 can include an integrated flashback chamber having an open proximal end that is closed to fluid flow by a vented plug which allows air but not fluid to flow therethrough. Needle hub 34 may be formed from the same types of materials that are used to form catheter adapter 24. Of course, other materials could be used to form needle hub 34.

In order to place catheter 21 into a patient's blood vessel, the clinician grasps the integrated catheter and introducer needle assembly to substantially longitudinally align introducer needle 31 and catheter 21 with the target blood vessel. The bevel of sharp distal tip 32 should be facing substantially away from the skin surface during venipuncture. The clinician inserts introducer needle 31 and catheter 21 at a shallow angle, preferably less than about 35 degrees, into the skin so that sharp distal tip 32 enters the target blood vessel. Where catheter 21, catheter adapter 24 and extension tube 25 are made from translucent material and notch 33 is formed in introducer needle 31, the clinician will be able to observe blood flashback along catheter 21, then in catheter adapter 24 and finally in extension tube 25. Alternatively, if a flashback chamber is located in needle hub 34 and no notch is formed in introducer needle 31, the clinician would observe blood flashback in a flashback chamber formed in needle hub 34.

After confirming placement of introducer needle 31 and catheter 21 in the target blood vessel, the clinician advances catheter 21 distally axially along introducer needle 31 into position in the blood vessel. In certain techniques, introducer needle 31 may be partially withdrawn into catheter 21 before catheter 21 is completely advanced into position in the blood vessel. After proper placement of catheter 21 is achieved, the clinician would normally have to place a finger from her other hand on the patient's skin over the blood vessel approximately over the distal end of catheter 21. By placing her finger on the patient's skin and applying sufficient pressure on the skin, the clinician would thereby substantially occlude or at least minimize blood flow through catheter 21. However, by using the low drag septum of this invention in an integrated catheter, the clinician would not need to apply this pressure because septum 29 would prevent blood from leaking from catheter assembly 20. The clinician then withdraws introducer needle 31 from catheter 21 by moving needle hub 34 proximally. Introducer needle 30 assembly is removed from catheter adapter 24 and disposed of according to the facility's disposal protocol. Again, because of septum 29, blood will not escape from catheter adapter 24. This allows the clinician ample time to attach a fluid delivery device, a PRN, a deadender cap or some other blood monitoring device to catheter assembly 20 and commence the planned treatment. The clinician can then bend wings 26 so they match the contour of the patient's skin and suture catheter assembly 20 to the patient's skin using suture holes 28. Alternatively, the clinician can tape catheter assembly 20 to the patient's skin.

Thus, it is seen that an IV catheter and introducer needle assembly is provided that minimizes blood leakage from the assembly during the insertion procedure, even where a notched introducer needle is used, that exerts a reduced drag force on the introducer needle when it is being withdrawn from the catheter and where the septum in the catheter assembly does not take a compression set about the needle so the septum effectively blocks the flow of fluid therethrough even after the introducer needle is removed from the catheter.

We claim:

1. A catheter and introducer needle assembly, comprising:

a catheter having a proximal end and a distal end;

a catheter adapter in fluid communication with the catheter and having a proximal end and a distal end connected to the proximal end of the catheter, the catheter adapter including a side port in fluid communication with the catheter adapter;

an introducer needle disposed, at least in part, within the catheter, the introducer needle having a proximal end and a distal end with an opening, wherein the introducer needle defines a notch therein adjacent to the distal end, and wherein a notch distance is defined as the distance between a proximal end of the notch and a distal end of the opening in the distal end of the introducer needle;

a needle hub having a proximal end and a distal end connected to the proximal end of needle; and an elastomeric septum having a distal portion and a proximal portion, the elastomeric septum being disposed in the catheter adapter and located proximal of the side port wherein the septum has a length greater than the notch distance.

2. The catheter and introducer needle assembly of claim 1 wherein the distal portion is radially compressed by the catheter adapter.

3. The catheter and introducer needle assembly of claim 2 wherein the catheter adapter is tapered at its proximal end.

4. The catheter and introducer needle assembly of claim 3 wherein the catheter adapter further comprises a housing extending along at least the distal portion of the septum.

5. The catheter and introducer needle assembly of claim 1 wherein the catheter adapter comprises a housing extending at least along the distal portion of the septum.

6. The catheter and introducer needle assembly of claim 1 wherein the proximal portion of the septum and the distal portion of the septum are two separate pieces.

7. The catheter and introducer assembly of claim 6 wherein a cavity is located in the septum, extending from the distal portion to the proximal portion.

8. The catheter and introducer assembly of claim 6 wherein the cavity is tapered radially outward from a distal end of the distal portion toward a proximal end of the distal portion.

9. The catheter and introducer assembly of claim 6 wherein the cavity is tapered radially outward from a proximal end of the proximal portion toward a distal end of the proximal portion.

10. The catheter and introducer assembly of claim 9 wherein the cavity is tapered radially outward from a distal end of the distal portion toward a proximal end of the distal portion.

11. A septum assembly, comprising:

a needle having a cross section;

a septum holder having a fixed shape; and a septum disposed in the septum holding and including a septum proximal portion and a septum distal portion and defining a cavity between the septum proximal portion and the septum distal portion;

wherein the septum is disposed about the needle, and wherein the cavity is sized to be larger than the cross section of the needle such that the septum contacts the needle only at the proximal portion of the septum and at the distal portion of the septum;

wherein the needle has a proximal end and a distal end with an opening, wherein the introducer needle defines a notch therein adjacent to the distal end, and wherein a notch distance is defined as the distance between a proximal end of the notch and a distal end of the opening in the distal end of the introducer needle and wherein the septum has a length greater than the notch distance.

* * * * *